(12) United States Patent
Dernbach et al.

(10) Patent No.: US 6,692,616 B2
(45) Date of Patent: Feb. 17, 2004

(54) METHOD FOR PURIFYING TRIMETHYLOLPROPANE, WHICH IS PRODUCED BY HYDROGENATION, BY MEANS OF CONTINUOUS DISTILLATION

(75) Inventors: Matthias Dernbach, Dossenheim (DE); Detlef Kratz, Heidelberg (DE); Achim Stammer, Freinsheim (DE); Harald Rust, Neustadt (DE); Gerhard Schulz, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/168,980

(22) PCT Filed: Dec. 21, 2000

(86) PCT No.: PCT/EP00/13105

§ 371 (c)(1),
(2), (4) Date: Jun. 26, 2002

(87) PCT Pub. No.: WO01/47847

PCT Pub. Date: Jul. 5, 2001

(65) Prior Publication Data

US 2002/0189926 A1 Dec. 19, 2002

(30) Foreign Application Priority Data

Dec. 28, 1999 (DE) .......................................... 199 63 435

(51) Int. Cl.$^7$ .............................. B01D 3/14; C07C 29/80
(52) U.S. Cl. ............................ 203/2; 203/14; 203/18; 203/78; 203/80; 203/77; 203/75; 203/91; 568/854; 568/853; 568/680
(58) Field of Search ............................ 203/73, 2, 74, 203/18, 77, 75, 86, 28–29, 99, 78, 91, 14, DIG. 19; 568/853, 854, 601, 680

(56) References Cited

U.S. PATENT DOCUMENTS 2,790,837 A * 4/1957 Robeson ..................... 568/853

(List continued on next page.)

FOREIGN PATENT DOCUMENTS

DE 287 251 2/1991

(List continued on next page.)

Primary Examiner—Virginia Manoharan
(74) Attorney, Agent, or Firm—Keil & Weinkauf

(57) ABSTRACT

A process is disclosed for the purification, by distillation, of trimethylolpropane originating from the hydrogenation of 2,2-dimethylolbutanal, said process including the following steps:
(a) reaction of n-butyraldehyde with formaldehyde in the presence of catalytic amounts of a tertiary amine, and hydrogenation of the resulting mixture to give a mixture containing trimethylolpropane;
(b) separation of water, methanol, trialkylamine and/or trialkylammonium formate by distillation;
(c) heating of the residue obtained in (b) under reduced pressure to a temperature at which TMP is volatile and compounds boiling above TMP are cleaved, in order to separate off, by distillation, TMP and compounds more volatile than TMP;
(d) distillation of the distillate obtained in (c) in order to separate off the more volatile compounds and recover pure TMP; and
(e) optional distillation of the TMP obtained in (d) in order to recover TMP with a low APHA color index.

A process is also disclosed in which trialkylammonium formate is distilled under mild conditions from crude mixtures of polyhydric alcohols, predominantly trimethylolpropane.

23 Claims, 1 Drawing Sheet

U.S. PATENT DOCUMENTS

| | | | |
|---|---|---|---|
| 3,097,245 A | | 7/1963 | Russell et al. ............... 260/635 |
| 4,594,461 A | | 6/1986 | Merger et al. ............... 568/853 |
| 5,149,861 A | * | 9/1992 | Merger et al. ............... 560/234 |
| 5,603,835 A | | 2/1997 | Cheung et al. ............. 210/639 |
| 5,763,690 A | * | 6/1998 | Salek et al. .................. 568/853 |
| 6,018,074 A | * | 1/2000 | Kratz et al. .................. 560/234 |
| 6,034,285 A | | 3/2000 | Doi et al. .................... 568/853 |
| 6,187,971 B1 | * | 2/2001 | Kratz et al. .................. 568/853 |
| 6,441,254 B1 | * | 8/2002 | Dobert et al. ............... 568/853 |

FOREIGN PATENT DOCUMENTS

| | | |
|---|---|---|
| DE | 45 078 | 5/1996 |
| DE | 198 48 568 | 4/1999 |
| DE | 198 48 569 | 4/1999 |
| EP | 0 142 090 | 5/1985 |
| GB | 1 290 036 | 9/1972 |
| WO | WO 97/17313 | 5/1997 |
| WO | WO 98/28253 | 7/1998 |
| WO | WO 01/47847 | 7/2000 |

* cited by examiner

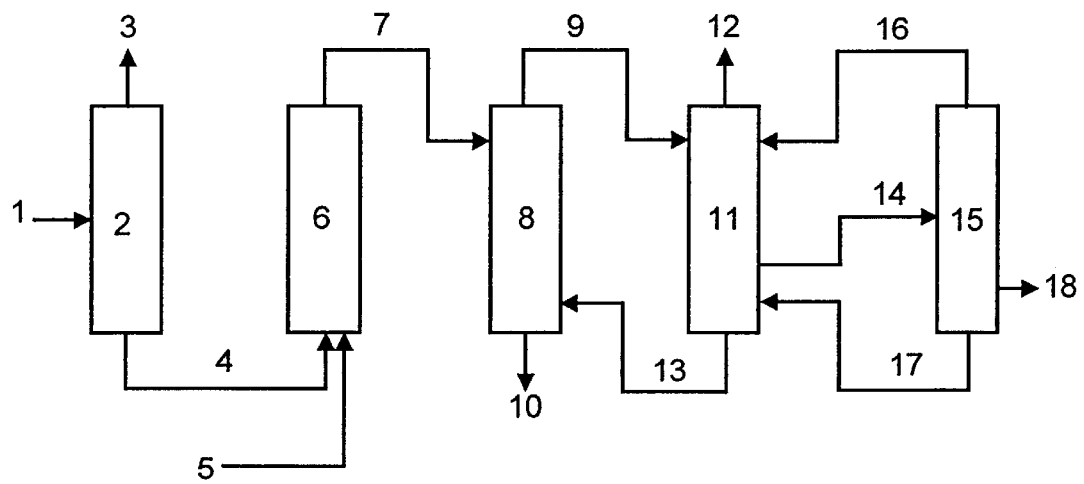

METHOD FOR PURIFYING TRIMETHYLOLPROPANE, WHICH IS PRODUCED BY HYDROGENATION, BY MEANS OF CONTINUOUS DISTILLATION

The present invention relates to the field of industrial chemistry. More precisely, it relates to a process in which trimethylolpropane obtained by the hydrogenation of dimethylolbutanal is purified by distillation. The present invention further relates to a process in which trialkylammonium formate produced as a by-product in the preparation of the alkylolated alkanal, from the trialkylamine used as catalyst and formic acid, can be separated off by simple distillation.

Trimethylolpropane, hereafter abbreviated to TMP, is a trihydric alcohol which has become widely used in the manufacture of surface coatings, polyurethanes and polyesters, for example alkyd resins. Trimethylolpropane is prepared by means of a condensation reaction between n-butyraldehyde and formaldehyde. This reaction can be carried out using different process variants.

Firstly, there is the so-called Cannizzaro process, in which the butyraldehyde is reacted with the formaldehyde in the presence of stoichiometric amounts of a base. 2,2-Dimethylolbutanal is formed in the first step and then reacts with excess formaldehyde, in a so-called crossed Cannizzaro reaction, to give formic acid and trimethylolpropane. The Cannizzaro process is referred to as inorganic or organic according to the type of base. The inorganic procedure employs an inorganic base, usually NaOH or Ca(OH)2. The disadvantage of this procedure is that a quantity of unwanted by-products is formed which are difficult to separate off and which interfere with the subsequent use of the trimethylolpropane. Also, one mole equivalent of formic acid salt is formed; this has to be discarded, thereby increasing the consumption of formaldehyde and contributing to environmental pollution.

In the organic Cannizzaro process, a tertiary amine, generally a trialkylamine, is used in place of the inorganic base. The reaction proceeds as described above to give one equivalent of the ammonium formate of the amine in question. This can be worked up further by appropriate measures, whereby at least the amine can be recovered and recycled into the reaction. The crude TMP obtained can be worked up to pure TMP in a variety of ways.

One further development is the hydrogenation process, in which butyraldehyde and formaldehyde are reacted together in the presence of catalytic amounts of a tertiary amine, generally approx. 5 to 10 mol %, rather than at least stoichiometric amounts. In this case the reaction stops at the 2,2-dimethylolbutanal stage and this compound is then converted to trimethylolpropane by hydrogenation. This method does not give rise to stoichiometric amounts of a formate, and the resulting solution is easier to purify because fewer interfering by-products are formed. In many cases, however, it is necessary to resort to reaction engineering measures to achieve a complete conversion of the educts to dimethylolbutanal. The description of an efficient process can be found in WO 98/28253 in the name of the Applicant.

The state of the art contains a wealth of publications describing different techniques for working up trimethylolpropane. A study of these publications clearly reveals the differences in work-up demanded by the different ways of preparing trimethylolpropane. The following publications relate to the purification of trimethylolpropane obtained by the inorganic Cannizzaro process.

DD-P-45 078 discloses a process in which the crude TMP obtained is treated with a secondary cycloaliphatic alcohol, for example cyclohexanol, water is then distilled off azeotropically with this alcohol and the formates which have precipitated are filtered off. After distillation of the excess alcohol, the crude product obtained is then purified by distillation.

DD-P-287 251 describes a process for freeing TMP of the high-boiling components formed. In the vacuum distillation of crude TMP, the high-boiling components accumulate in the fractions less volatile than TMP. Many of the high-boiling components, which consist of secondary reaction products of TMP, especially formals, can be converted back to TMP by the addition of 0.02 to 0.05 kg acid/kg distillate, thereby increasing the yield.

Also, GB 1 290 036 describes a process for the decomposition of TMP formals in crude batches obtained by the inorganic Cannizzaro process. By the addition of cation exchange resins and heating, formals contained in the crude mixtures, which have a similar boiling point to TMP, are converted to products of different boiling points which can readily be separated off by distillation. Pure TMP can be obtained.

U.S. Pat. No. 3,097,245 describes a process for the preparation of trimethylolpropane with an APHA color index of between 50 and 200. This color index is achieved by maintaining specific reaction conditions in respect of temperature, reaction time, pH and concentration of the starting compounds. The reaction is followed by treatment of the resulting solution with ion exchange resins.

U.S. Pat. No. 5,603,835 discloses a process for the preparation of TMP with APHA color indices of <100. These are achieved by extractive aftertreatment of the crude TMP solutions obtained with an ether or an ester. The TMP solutions used generally originate from the inorganic Cannizzaro process.

By contrast, crude TMP originating from the organic Cannizzaro process is worked up differently.

EP-B-142 090 describes the work-up of such a crude TMP mixture. This crude mixture is worked up by distillation and then hydrogenated and distilled again. Such a process is expensive, demands a high vacuum and gives low yields.

In particular, in the preparation of TMP by the organic Cannizzaro process, there is an interfering secondary reaction which can markedly reduce the yield of TMP. The trialkylammonium formate produced in the reaction reacts under specific conditions, for example dehydration of the solution or heating, to give trialkylamine and trimethylolpropane formates. These compromise the yield of trimethylolpropane and should therefore be cleaved as completely as possible without the simultaneous appearance of unwanted secondary reactions.

WO 97/17313 discloses a process suitable for this purpose. In the first step, trimethylolpropane is prepared in a manner known per se by reacting formaldehyde with butyraldehyde in the presence of stoichiometric amounts of a tertiary amine. In the second step, the crude TMP mixture is freed of excess water, tertiary amine and formaldehyde. In the third step, the residual mixture is heated, causing the cleavage of the trialkylammonium formate into trialkylamine and formic acid (both of which are separated off) and the formation of TMP formates. In the fourth step, the amine which has been separated off is recycled, either into the first step or into the fifth step which follows. In this fifth step, the TMP formate obtained is reacted with a lower alcohol (this reaction being catalyzed by the very amine which has been separated off) to free the TMP with the formation of methyl formate.

A similar process is disclosed in DE-A-198 48 568. The crude TMP mixture obtained after the conventional reaction in the presence of stoichiometric amounts of a trialkylamine is heated, freed of trialkylamine and, before work-up by distillation, treated with either water, ammonia, a primary amine or a secondary amine. The trimethylolpropane formate produced on heating is converted to TMP and formic acid or a formamide. The yield of TMP is increased.

However, the abovementioned processes are only of limited suitability for the efficient work-up of a TMP mixture obtained by the so-called hydrogenation process, in which only catalytic amounts of trialkylamine are used and which consequently also contains only small amounts of trialkylammonium formate.

It is therefore an object of the present invention to provide such a process. This process should furthermore make it possible to prepare TMP with a high purity, preferably >99%, with a low color index of 10 to 100 APHA and in high yield.

We have found that this object is achieved by a process for the purification, by distillation, of trimethylolpropane originating from the hydrogenation of 2,2-dimethylolbutanal, said process comprising the following steps:

a) reaction of n-butyraldehyde with formaldehyde in the presence of catalytic amounts of a tertiary amine, and hydrogenation of the resulting mixture to give a mixture containing trimethylolpropane;

b) separation of water, methanol, trialkylamine and/or trialkylammonium formate by distillation;

c) heating of the residue obtained in b) to a temperature at which trimethylolpropane is volatile and compounds boiling above trimethylolpropane are at least partially cleaved, in order to separate off, by distillation, trimethylolpropane and compounds more volatile than trimethylolpropane;

d) distillation of the distillate obtained in c) in order to separate off the more volatile compounds and recover pure trimethylolpropane; and e) optional distillation of the trimethylolpropane obtained in d) in order to recover TMP with a low APHA color index.

We have also found that this object is achieved by a generally applicable process for removing trialkylammonium formates from polyhydric alcohols obtained by condensing formaldehyde with a higher aldehyde, wherein the trialkylammonium formate, together with methanol, trialkylamine and optionally water, is distilled from the alcohol at pressures of <400 mbar, preferably 20 to 200 mbar, and particularly preferably 40 to 150 mbar, and at bottom temperatures of <200° C., preferably 60 to 140° C., and particularly preferably 80 to 120° C., and with short residence times. The polyhydric alcohol is trimethylolpropane in particular.

Within the framework of the process according to the invention for the purification of trimethylolpropane by distillation, crude TMP solutions which have been prepared by the so-called hydrogenation process are purified. In other words, the TMP has been obtained by condensing n-butyraldehyde with formaldehyde in the presence of catalytic amounts of a tertiary amine, this being followed by catalytic hydrogenation of the dimethylolbutanal mixture formed. Thus the crude TMP contains no alkali metal or alkaline earth metal formates or other impurities produced in the inorganic Cannizzaro process. Similarly, in contrast to the organic Cannizzaro process, the crude TMP contains only small amounts of approx. 5 to 10 mol % of trialkylammonium formates or free trialkylamine.

In addition to trimethylolpropane and water, the crude TMP which originates from hydrogenation and is to be subjected to the purification process according to the invention also contains methanol, trialkylamine, trialkylammonium formate, longer-chain linear and branched alcohols and diols, for example methylbutanol or ethylpropanediol, addition products of formaldehyde and methanol with trimethylolpropane, acetals, such as dimethylolbutyraldehyde TMP acetal, and so-called di-TMP.

Good results have been achieved with hydrogenation discharges containing 10 to 40% by weight of trimethylolpropane, 0.5 to 5% by weight of methanol, 1 to 6% by weight of methylbutanol, 1 to 10% by weight of trialkylammonium formate, 0 to 5% by weight of 2-ethylpropanediol, 2 to 10% by weight of high-boiling components, such as di-TMP or other addition products, and 5 to 80% by weight of water. Hydrogenation discharges of such a composition can be obtained for example by the process described in WO 98/28253.

In process step b) following hydrogenation, the hydrogenation discharge is then subjected to distillation, in which water and other readily volatile compounds, such as methanol, trialkylamine and optionally trialkylammonium formate, are separated off. This distillation is carried out with the apparatuses familiar to those skilled in the art, for example evaporators and/or distillation columns, the pressures used being 20 mbar to 1 bar. The composition of the bottom mixture obtained after distillation is very dependent on the conditions under which the distillation step has been carried out.

If this distillation is carried out under mild conditions, the trialkylammonium formate present in the solution distils off with the other low-boiling components mentioned above, and only small amounts of TMP formates are produced, if any, as described previously. In the context of the present invention, mild conditions are low pressures of <400 mbar, preferably 20 to 200 mbar and particularly preferably 40 to 150 mbar, and bottom temperatures of <200° C., preferably 60 to 140° C. and particularly preferably 80 to 120° C. Under these conditions and when using appropriate apparatuses, it is possible to achieve the short residence times necessary to suppress further reaction of the trialkylammonium formate. Short residence times according to the invention range from 5 min to 2 h. Apparatuses which allow such short residence times to be observed are, for example, film evaporators, falling film evaporators or spiral tube evaporators. These apparatuses can be operated with or without an attached distillation column.

Under the conditions described, trialkylammonium formate can be separated from trimethylolpropane mixtures without a significant degree of decomposition being observed. Under suitable reaction conditions, approximately at least 95% of the amount of trialkylammonium formate present can be distilled off at the top. Thus trimethylolpropane formate is only formed in amounts which do not exceed approximately 5%, based on the amount of trialkylammonium formate.

In one variant, the trialkylammonium formate can be separated off in such a way that, in a first step (bi), water is initially separated from the reaction mixture under extremely mild conditions, the water being entrained so as to reduce the residual water content of the mixture to below 10% by weight, preferably below 5% by weight. The decomposition reaction of the trialkylammonium formate can thereby be further suppressed. The initial separation of water is then followed, in a second step (bii), by distillation of the other low-boiling components and the trialkylammonium formate, as described above.

The separation of trialkylammonium formate by distillation is particularly advantageous in the purification of crude trimethylolpropane mixtures. Of course, this distillative separation according to the invention can also be carried out in connection with the synthesis of other polyhydric alcohols obtained by condensing formaldehyde with higher aldehydes in the presence of trialkylamines. A condition is that the boiling point of the polyhydric alcohol is not too close to that of the trialkylammonium formate, thereby allowing the latter to be separated off by distillation. Also, of course, the polyhydric alcohol must not decompose under the conditions used in the distillation.

The distillative separation of trialkylammonium formate according to the invention is particularly suitable in the case of polyhydric alcohols which have been prepared by the hydrogenation process. The relatively small amounts of trialkylammonium formate obtained in this process, being at most approx. 10 mol % based on the alcohol, can thus be efficiently separated off and correspondingly small amounts of alcohol formates are produced. However, the process according to the invention can also be used for polyhydric alcohols which have been prepared by the organic Cannizzaro process. The large amounts of trialkylammonium formate produced in this case frequently demand a greater expenditure on apparatus for the distillation.

The distillative separation according to the invention can be carried out batchwise or continuously. The evaporator can be operated without or, preferably, with a recycle stream.

If, on the other hand, water and the other low-boiling components are distilled off at pressures of >200 mbar, preferably >400 mbar, and bottom temperatures of >140° C., preferably 160 to 185° C., a reaction takes place between the trialkylammonium formate and trimethylolpropane to give trialkylamine and formates of the trimethylolpropane. The formation of these formates is also favored by long residence times. If this procedure is chosen, the trialkylamine formed distils off with the other low-boiling components and can be re-used in the aldolization reaction. The bottom product obtained after distillation then contains approx. 2 to 10% by weight of trimethylolpropane formate.

If process step (b), i.e. the dehydration of the crude discharge, is carried out under conditions where trimethylolpropane formates are produced, step (b) is followed by a process step (bb), in which these formates are cleaved and TMP is recovered.

This can be effected in a manner known per se, for example by carrying out a transesterification with a lower alcohol, for example methanol, to give formates of this alcohol and TMP. This transesterification can be carried out for example as described in EP-A-289 921, in the presence of catalytic amounts of alkali metal or alkaline earth metal alcoholates. The reaction can also be carried out as disclosed in WO 97/17313, where a tertiary amine is used to catalyze the reaction. The reaction can also be catalyzed by acid.

Another possible way of freeing trimethylolpropane from its formates is to react them with an anhydrous secondary amine, as described in the German patent application entitled "Verfahren zur Umwandlung von bei der Trimethylolalkan-Herstellung anfallenden Trimethylolalkanformiat" ["Process for converting trimethylolalkane formate obtained in the preparation of trimethylolalkane"] (Applicant: BASF AG).

In process step (c), the residue originating from step (b) or (bb) is then heated to a temperature at which the so-called high-boiling components, i.e. compounds less volatile than TMP, are separated off. This heating takes place under reduced pressures of 5 to 50 mbar, preferably 10 to 30 mbar, the bottom temperatures being 210 to 250° C., preferably 220 to 235° C. Under these conditions the TMP distils off together with other compounds more volatile than TMP, i.e. the so-called low-boiling components. In connection with the present invention, it is important that the high temperatures at the bottom of the column cause the cleavage of some of the high-boiling components which are TMP derivatives, examples being dimethylolbutyraldehyde TMP acetal and higher acetals. The decomposition of the high-boiling components can be accelerated by suitable measures known per se, for example the addition of acid. This makes it possible to increase the yield of TMP even further. It is particularly advantageous to add acid according to the process described in the German patent application entitled "Verfahren zum Zersetzen von bei der Synthese mehrwertiger Alkohole gebildeter hochsiedender Nebenprodukte" ["Process for decomposing high-boiling by-products formed in the synthesis of polyhydric alcohols"], reference no. 199 63 437.8 (Applicant: BASF AG). This gives a bottom product containing 1 to 50% by weight of TMP. In process step (c), the low-boiling components and the TMP are distilled together from the impurities remaining in the bottom product, and are collected. The distillation is generally carried out by means of a column with a reflux ratio of 0 to 3, preferably 0 to 1. The conventional internals known to those skilled in the art, preferably regularly spaced packings, are used in the column.

The distillate originating from step (c), which contains TMP and the so-called low-boiling components, for example 2-ethylpropanediol or TMP formate, is then purified by distillation in step (d). This distillation is generally carried out in a column. The low-boiling components are separated off at the top and the TMP is withdrawn from the column as a side discharge, preferably below the feed. The side discharge can be liquid, although it is preferably gaseous.

A TMP with a purity of <99% and an APHA color index of 20 to 200 can be obtained by this method. The distillation is carried out in the conventional columns known to those skilled in the art, preferably columns equipped with internals. Regular packings are preferably used. The distillation is carried out at pressures of 10 to 40 mbar, preferably 20 to 30 mbar, and at bottom temperatures of 170 to 210° C., preferably 180 to 200° C. It has proved advantageous to extract a small stream from the bottom of the column in order to prevent an accumulation of high-boiling and/or colorizing components.

In the variant of the present invention, steps (b) and (d) can be combined. In this case the mixture obtained after hydrogenation in step (a) is distilled in such a way that not only the very readily volatile compounds, such as water, methanol and triethylamine, but also the other so-called low-boiling components are distilled off, which in principle, as described previously, are not removed until after the high-boiling components have been separated from the TMP. Examples of said low-boiling components are 2-ethylpropanediol or TMP formates, although often some of these have also already passed over with the very readily volatile compounds. To achieve this complete separation of the compounds more volatile than TMP, said separation is carried out at pressures of 10 to 40 mbar and temperatures of 170 to 210° C. It can be carried out in evaporators, but it is preferable to use distillation columns because the distillation of TMP can be prevented in this way.

In another variant of the invention, steps (c) and (d), i.e. the joint distillative separation of TMP and low-boiling components from the high-boiling components and the subsequent distillative separation of the low-boiling components from TMP, can be carried out in a single step. To do this, when the mixture withdrawn from step (b) is heated under the abovementioned conditions, the volatile compounds have to be distilled off over a column of appropriate separation efficiency and separated with said column. It is advantageous to use columns with a side discharge, i.e. ones which are also used when carrying out step (d) separately from step (c).

The TMP withdrawn from step (d), i.e. from the purification by distillation to separate off the low-boiling components, can be subjected to a second purification by distillation (e). This second distillation is optional and serves to improve the color index in cases where it is desired to obtain, as far as possible, a colorless TMP. It may be said that the distillation (d) is carried out in order to obtain a pure product. The distillation (e) affords virtually no further improvement in the purity, only in the color index.

The distillation is generally carried out in a column. Lower-boiling colorizing components are separated off at the top and the TMP is withdrawn from the column as a side discharge, preferably below the feed. The side discharge can be liquid, although it is preferably gaseous.

This procedure makes it possible to obtain a TMP with color indices of 10 to 100 APHA. The distillation is performed in the customary columns known to those skilled in the art, preferably in columns equipped with internals. The preferred internals are regularly spaced packings. The distillation is carried out at pressures of 5 to 40 mbar, preferably 20 to 30 mbar, and at bottom temperatures of 170 to 210° C., preferably 180 to 200° C. It has proved advantageous here to extract a small stream from the bottom of the column so as to prevent an accumulation of higher-boiling and/or colorizing components.

The process according to the invention will now be explained with reference to the diagram shown in FIG. 1, which illustrates one particular variant of the process.

The crude TMP solution 1 obtained after the condensation reaction and subsequent hydrogenation is introduced into the low-boiling column 2, in which a mixture 3 of water and low-boiling components, such as methanol or trialkylamine, is separated off. After purification, this dialkylamine can be re-used as a catalyst in the condensation reaction between n-butyraldehyde and formaldehyde. The bottom product 4 withdrawn from the low-boiling column, which contains TMP, high-boiling components and the low-boiling components not separated off in the column 2, is introduced into the reactor 6, in which trimethylolpropane formates are cleaved. This is effected by adding a dialkylamine or an alcohol, for instance methanol, denoted by the number 5. The conversion of the TMP formates to TMP and either formates of the alcohol used or formamides of the amine used takes place in the reactor 6. The use of the reactor 6 for cleavage of the formates is optional. This reactor is not used if the conditions in the low-boiling column 2 are chosen so that no TMP formates are produced from trialkylammonium formate and free TMP.

The solution 7, depleted in TMP formates, now passes into the high-boiling separator 8, in which the solution 7 is heated under reduced pressure to temperatures at which a mixture 9 of TMP and more volatile substances is distilled off. At the same time, high-boiling components which are TMP derivatives are decomposed by the high temperatures. These then also distil off with the mixture 9 and increase the yield of TMP. This leaves a bottom product 10 rich in high-boiling components. Said bottom product 10 is discarded or can be combusted to raise superheated steam. It can also be distilled further in order to purify particular compounds.

The mixture 9 of TMP and low-boiling components is then introduced into the first distillative purification unit 11, where the impurities 12 boiling below TMP are separated off at the top. They can be discarded, combusted to raise superheated steam or purified further to recover individual components contained therein. A stream 13 of colorizing and high-boiling components is extracted from the distillative purification unit 11 and can be recycled into the high-boiling separator 8 or else discarded. Finally, the pure TMP 14 withdrawn from the unit 11 is subjected to an (optional) distillation in a color index distillation device 15, where the lower-boiling colorizing components 16 are distilled off at the top. They can be discarded or recycled into the distillative purification unit 11. High-boiling and colorizing components 17 which accumulate slowly at the bottom of the device 15 are extracted and discarded or recycled into the distillative purification unit. A pure TMP 18 with a low color index is recovered.

The present invention will now be illustrated with the aid of the examples below. The trimethylolpropane used in all the examples had been prepared as follows:

An apparatus consisting of two heatable stirred tanks with an overall capacity of 72 l, interconnected by overflow tubes, was charged continuously with fresh aqueous formaldehyde solution (4300 g/h in the form of a 40% aqueous solution) and n-butyraldehyde (1800 g/h), and with fresh trimethylamine as catalyst (130 g/h) in the form of a 45% aqueous solution. The reactors were heated to a constant temperature of 40° C.

The discharge was passed directly into the top of a falling film evaporator with attached column (superheated steam at 11 bar), where it was separated by distillation under atmospheric pressure into a low-boiling top product, essentially containing n-butyraldehyde, ethylacrolein, formaldehyde, water and trimethylamine, and a high-boiling bottom product.

The top product was continuously condensed and recycled into the reactors described above.

The high-boiling bottom product from the evaporator (approx. 33.5 kg/h) was treated continuously with fresh trimethylamine catalyst (50 g/h, in the form of a 45% aqueous solution) and transferred to a heatable, packed tubular reactor with an empty volume of 12 l. The reactor was heated to a constant temperature of 40° C.

The discharge from the secondary reactor was passed continuously into the top of another distillation device for separation of the formaldehyde (superheated steam at 11 bar), where it was separated by distillation into a low-boiling top product, essentially containing ethylacrolein, formaldehyde, water and trimethylamine, and a high-boiling bottom product. The low-boiling top product (27 kg/h) was continuously condensed and recycled into the first stirred tank, while the high-boiling bottom product was collected.

In addition to water, the resulting bottom product contained essentially dimethylolbutyraldehyde, formaldehyde and traces of monomethylbutyraldehyde. This bottom product was then subjected to continuous hydrogenation. This was done by hydrogenating the reaction solution at 90 bar and 115° C. in a primary reactor by the loop/trickle method and in a downstream secondary reactor by the loop method. The catalyst was prepared analogously to D of DE 198 09 418. It contained 24% of CuO, 20% of Cu and 46% of $TiO_2$. The apparatus used consisted of a heated primary reactor with a length of 10 m (internal diameter: 27 mm) and a heated secondary reactor with a length of 5.3 m (internal diameter: 25 mm). The loop throughput was 25 l/h of liquid and the reactor feed was adjusted to 4 kg/h, corresponding to a hydrogenation discharge of 4 kg/h.

EXAMPLE 1

The TMP used had a composition of 22.6% by weight of TMP, 1.4% by weight of methanol, 2.1% by weight of trimethylammonium formate, 1.1% by weight of methylbutanol, 0.7% by weight of ethylpropanediol, 1.2% by weight of adducts of TMP with formaldehyde and methanol, <0.1% of TMP formate, 1.2% by weight of TMP dimethylbutanal acetals, 2.9% by weight of high-boiling components and 66.2% by weight of water. 5 kg/h of this crude solution were worked up. The crude mixture was first dehydrated in the low-boiling column at 400 mbar and a bottom temperature of 160° C., the feed entering the middle of the column. The reflux ratio was adjusted to 0.3. 1.3 kg/h of a mixture consisting of 83% by weight of TMP, higher-boiling impurities, approx. 1% by weight of water and 7.5% by weight of TMP formates were withdrawn from the bottom of the column and transferred to the high-boiling separator. This consisted of a column operated at 20 mbar and a reflux ratio of 0.5. High-boiling components containing 24.4% by weight of TMP were thus separated off at the bottom of the column. The TMP freed of high-boiling components is withdrawn from the top and purified in a distillation unit consisting of a column with a side discharge point, operated at 20 mbar with temperature-regulated reflux. The components boiling below TMP, such as 2-ethylpropanediol and TMP formate (20.7% by weight), are distilled off at the top, the distillate having a residual TMP content of 6.6% by weight. To prevent the accumulation of high-boiling components, 150 g/h are withdrawn from the bottom of the column and recycled into the high-boiling separation stage. Pure TMP with a content of >99% is withdrawn from the vaporous side discharge above the evaporator in an amount of 1030 g/h. The overall yield of the work-up is 90%.

EXAMPLE 2

TMP was prepared as described in Example 1 and had a composition of 22.1% by weight of TMP, 0.4% by weight of methanol, 1.5% by weight of trimethylammonium formate, 0.7% by weight of methylbutanol, 0.5% by weight of ethylpropanediol, 1.2% by weight of adducts of TMP with formaldehyde and methanol, <0.1% by weight of TMP formate, 1.4% by weight of acetals of TMP with dimethylbutanal, 2.2% by weight of high-boiling components and 69.9% by weight of water. The throughput was 4 kg/h. The crude mixture was first introduced into the low-boiling column, dehydration being carried out at 400 mbar and 180° C. The feed entered the middle of the column. The reflux ratio was adjusted to 0.3. 1.1 kg/h of dehydrated TMP, containing 82.8% by weight of TMP, higher-boiling impurities, approx. 0.5% by weight of water and 6.6% by weight of TMP formate, were withdrawn from the bottom of the column, mixed with 40 g/h of dimethylamine and introduced into a tubular reactor in which the TMP formate is reacted with dimethylamine at 120° C. and with a residence time of 1 hour to give TMP and dimethylformamide. The resulting conversion was 95%, making it possible to lower the residual content of TMP formate to <0.3% by weight. The reaction discharge obtained was introduced into the high-boiling separation device, where the high-boiling components were separated off at 30 mbar and a reflux ratio of 0. High-boiling components with a residual TMP content of 10% by weight were thus separated off at the bottom of the column. During the separation, 85% phosphoric acid is introduced batchwise into the bottom of the column to give a phosphoric acid concentration of between 100 ppm and 1000 ppm. TMP freed of high-boiling components is distilled off at the top and then purified by distillation carried out at 30 mbar and with temperature-regulated reflux in a column with a side discharge point. In this distillative purification, compounds boiling below TMP, such as 2-ethylpropanediol or TMP formate, are distilled off at the top to give a top product with a residual TMP content of 7% by weight. A discharge with a TMP content of >98% by weight is withdrawn from the bottom of the column in an amount of 150 g/h and recycled into the high-boiling separator. Pure TMP with a content of >99% is withdrawn from the vaporous side discharge above the evaporator. The overall yield of the work-up is 98%, the TMP obtained having color indices of between 30 and 150 APHA.

EXAMPLE 3

The procedure was as described in Example 2. To improve the color index, the pure TMP obtained was then subjected to a further distillation in a column with a side discharge point. This color index distillation was carried out at 20 mbar and a reflux ratio of 35. 150 g/h of bottom discharge with a TMP content of >98% and 30 g/h of top discharge with a TMP content of >98% were recycled into the distillative purification stage. A pure colorless TMP with a color index of 15 to 50 APHA was withdrawn from the vaporous side discharge above the evaporator.

EXAMPLE 4

The TMP used had a composition of 1.59% of trimethylammonium formate, 27.0% of trimethylolpropane and 69% of water, the remainder being by-products, and was free of trimethylolpropane formate. This TMP (3500 g) was then pumped at 50 mbar and a rate of 600 ml/h into a Sambay evaporator at a Sambay temperature of 180° C. The bottom and top products were withdrawn. The bottom discharge was taken from a recycle stream of 6.2 l/h. The bottom product (993 g) had a composition of 92.2% of TMP, 0.31% of trimethylammonium formate, 0.55% of trimethylolpropane formate and 0.49% of water, the remainder consisting of other by-products. This bottom product can be worked up further as described in one of Examples 1 to 3. The top product (2498 g) had a composition of 2.1% of trimethylammonium formate, 2.1% of TMP and 95.9% of water and was free of trimethylolpropane formate. 94% of the trimethylammonium formate could thus be separated off at the top.

We claim:
1. A process for purifying a polyhydric alcohol obtained by condensing formaldehyde with a higher aldehyde, which process comprises
   i) providing a crude polyhydric alcohol comprising trialkylammonium formate, methanol, trialkylamine and optionally water, and obtained by condensing formaldehyde with a higher aldehyde, and
   ii) separating the crude polyhydric alcohol into a first fraction comprising the polyhydric alcohol and a second fraction comprising trialkylammonium formate, methanol, trialkylamine and optionally water, by means of a distillation,
   wherein the distillation is conducted under conditions adapted to suppress a reaction of trialkylammonium formate, at a bottom temperature of >200° C., at a pressure of >400 mbar, and with a residence time of from 5 minutes to 2 hours.

2. The process of claim 1, wherein the crude polyhydric alcohol is obtained by initially condensing formaldehyde and the higher aldehyde to form an, alkcylolated alkanal, and subsequently hydrogenating the alkylolated alkanal.

3. The process of claim 2, wherein the alkylolated alkanal is dimethylolbutanal and the polyhydric alcohol is trimethylolpropane.

4. The process of claim 1, wherein the crude polyhydric alcohol comprises water, and stage (ii) is conducted by firstly removing water to obtain a crude polyhydric alcohol which has a water content of less than 10% by weight, and subsequently removing trialkylammonium formate and other impurities.

5. The process of claim 1, wherein the bottom temperature is 60 to 140° C.

6. The process of claim 1, wherein the pressure is 20 to 200 mbar.

7. The process of claim 1, wherein the second fraction comprises at least approximately 95% of the trialkylammonium formate present in the crude polyhydric alcohol.

8. A process for purifying a trimethylolpropane obtained by hydrogenating a 2,2-dimethylolbutanal, which process comprises the steps of:
(a) reacting n-butyraldehyde with formaldehyde in the presence of catalytic amounts of tertiary amine to obtain a crude 2,2-di-methylolbutanal, and hydrogenating the crude 2,2-dimethylolbutanal to obtain a trimethylolpropane mixture comprising, as impurities, water, methanol, trialkylamine and/or trialkylammonium formate;
(b) separating the trimethylolpropane mixture obtained in (a) into a first fraction consisting essentially of impurities, and a first residue comprising the trimethylolpropane and residual impurities by means of a distillation;
(c) heating the first residue obtained in (b) at a reduced pressure to a temperature at which trimethylolpropane is volatile and constituents of the first residue which have a boiling point higher than trimethylolpropane are cleaved, and distilling off from the heated residue at the reduced pressure a second fraction comprising trimethylolpropane and residual compounds which are more volatile than trimethylolpropane;
(d) subjecting the second fraction obtained in (c) to a distillation wherein the residual compounds are distilled off to obtain a trimethylolpropane fraction having a purity of at least 99%; and optionally
(e) subjecting the trimethylolpropane fraction obtained in (d) to a further distillation to obtain a trimethylolpropane having an improved APHA color index.

9. The process of claim 8, wherein the distillation in (b) is carried out at a pressure of >400 mbar, at a bottom temperature of >200° C., and with a residence time of 5 minutes to 2 hours, in such a way that at most approximately 5% of trialkylammonium formate which is present in the trimethylolpropane mixture obtained in (a) react with trimethylolpropane to give trimethylolpropane formates and trialkylamine.

10. The process of claim 9, wherein the distillation in (b) is carried out at from 20 to 200 mbar.

11. The process of claim 9, wherein the bottom temperature in the distillation in (b) is 60 to 140° C.

12. The process of claim 8, wherein (b) comprises the steps of:
(bi) initially removing water which is present in the trimethylolpropane mixture obtained in (a) to reduce the water content of the mixture to an amount of less than 10%; and
(bii) subsequently removing trialkylammonium formate which is present in the trimethylolpropane mixture obtained in (a) and remaining impurities which are more volatile than trimethylolpropane.

13. The process of claim 8, wherein the distillation in (b) is carried out at a pressure of <200 mbar, at a bottom temperature of <140° C., and with residence times adapted to allow for a reaction of the trimethylolpropane and trialkylammonium formate which is present in the trimethylolpropane mixture obtained in (a) to form trimethylolpropane formates and trialkylamine.

14. The process of claim 13, wherein after step (b) and prior to step (c) the trimethylolpropane formates are reacted with a lower alcohol or with a secondary amine to obtain trimethylolpropane and a formate of the lower alcohol or a formamide of the secondary amine.

15. The process of claim 14, wherein the lower alcohol is methanol and the secondary amine is a dialkylamine.

16. The process of claim 13, wherein the distillation in (b) is carried out at <400 mbar.

17. The process of claim 13, wherein the bottom temperature in the distillation in (b) is 160 to 185° C.

18. The process of claim 8, wherein step (c) is carried out at a bottom temperature of 210 to 250° C., and at a pressure of 5 to 50 mbar.

19. The process of claim 8, wherein step (d) is carried out at a bottom temperature of 170 to 210° C., and at a pressure of 10 to 40 mbar.

20. The process of claim 8, wherein the trimethylolpropane fraction obtained in (d) is subjected to the distillation step (e) and the distillation is carried out at a bottom temperature of 170 to 210° C., and at a pressure of 5 to 40 mbar.

21. The process of claim 8, wherein the distillation in (b) is carried out at a pressure of 10 to 40 mbar and at a temperature of 170 to 210° C. to achieve a complete separation of all compounds which are more volatile than trimethylolpropane.

22. The process of claim 8, wherein the distillations in (c) and (d) are combined to one distillation which comprises separating the residue obtained in (b) into a bottom fraction consisting essentially of components which are less volatile than trimethylolpropane, a top fraction consisting essentially of compounds which are more volatile than trimethylolpropane, and a trimethylolpropane fraction having a purity of at least 99%.

23. The process of claim 8, wherein the trimethylolpropane fraction obtained in (d) is subjected to the distillation step (e).

* * * * *

UNITED STATES PATENT AND TRADEMARK OFFICE
CERTIFICATE OF CORRECTION

PATENT NO. : 6,692,616 B2
DATED : February 17, 2004
INVENTOR(S) : Dernbach et al.

It is certified that error appears in the above-identified patent and that said Letters Patent is hereby corrected as shown below:

Title page,
Item [57], ABSTRACT, should read as follows:

```
A crude trimethylolpropane mixture which is obtained by
(a) reacting n-butyraldehyde with formaldehyde in the presence of
    catalytic amounts of a tertiary amine to obtain a crude 2,2-dime-
    thylolbutanal, and subsequent hydrogenation of the crude 2,2-di-
    methylolbutanal;
is purified by
(b) initially distilling off water, methanol, trialkylamine and/or
    trialkylammonium formate;
(c) then heating the residue obtained in (b) under reduced pressure
    to a temperature at which TMP is volatile and compounds boiling
    above TMP are cleaved, and distilling off a fraction containing
    TMP and compounds more volatile than TMP; and
(d) subjecting the TMP fraction obtained in (c) to a further dis-
    tillation in which the more volatile compounds are removed and
    purified TMP is recovered.
The APHA color index of the purified TMP can be improved by subject-
ing the purified TMP obtained in (d) to an additional distillation.
Correspondingly, trialkylammonium formate can be separated from crude
mixtures of polyhydric alcohols such as trimethylolpropane by dis-
tillation under mild conditions.
```

Column 11,
Line 1, ">" should be -- < --.
Line 6, "alkcylolated" should be -- alkylolated --.
Lines 56 and 57, ">" should be -- < --.

UNITED STATES PATENT AND TRADEMARK OFFICE
CERTIFICATE OF CORRECTION

PATENT NO. : 6,692,616 B2
DATED : February 17, 2004
INVENTOR(S) : Dernbach et al.

It is certified that error appears in the above-identified patent and that said Letters Patent is hereby corrected as shown below:

Column 12,
Lines 17 and 18, "<" should be -- > -- .
Lines 31, "<" should be -- > -- .

Signed and Sealed this

Fifteenth Day of June, 2004

JON W. DUDAS
*Acting Director of the United States Patent and Trademark Office*